United States Patent
Bruns et al.

(10) Patent No.: US 9,051,243 B2
(45) Date of Patent: Jun. 9, 2015

(54) PROCESS FOR THE PREPARATION OF ISOCYANATES IN THE GAS PHASE

(75) Inventors: Rainer Bruns, Leverkusen (DE); Wolfgang Lorenz, Dormagen (DE); Andreas Karl Rausch, Neuss (DE)

(73) Assignee: Bayer MaterialScience AG, Leverkusen (DE)

(*) Notice: Subject to any disclaimer, the term of this patent is extended or adjusted under 35 U.S.C. 154(b) by 0 days.

(21) Appl. No.: 13/383,936

(22) PCT Filed: Jul. 6, 2010

(86) PCT No.: PCT/EP2010/004109
§ 371 (c)(1),
(2), (4) Date: Jan. 13, 2012

(87) PCT Pub. No.: WO2011/006609
PCT Pub. Date: Jan. 20, 2011

(65) Prior Publication Data
US 2012/0108845 A1    May 3, 2012

(30) Foreign Application Priority Data
Jul. 17, 2009  (DE) .......................... 10 2009 033 639

(51) Int. Cl.
*C07C 263/10*    (2006.01)
(52) U.S. Cl.
CPC .................................. *C07C 263/10* (2013.01)

(58) Field of Classification Search
None
See application file for complete search history.

(56) References Cited

U.S. PATENT DOCUMENTS

| 4,847,408 | A | 7/1989 | Frosch et al. | |
|---|---|---|---|---|
| 5,391,683 | A | 2/1995 | Joulak et al. | |
| 5,449,818 | A | 9/1995 | Biskup et al. | |
| 6,974,880 | B2 | 12/2005 | Biskup et al. | |
| 7,019,164 | B2 | 3/2006 | Freidrich et al. | |
| 7,541,487 | B2 | 6/2009 | Pohl et al. | |
| 2007/0043233 | A1 | 2/2007 | Sanders et al. | |
| 2008/0146834 | A1* | 6/2008 | Pohl et al. | 560/347 |
| 2010/0041914 | A1 | 2/2010 | Woelfert et al. | |
| 2010/0312009 | A1* | 12/2010 | Sanders et al. | 560/347 |
| 2011/0301380 | A1 | 12/2011 | Knoesche et al. | |

OTHER PUBLICATIONS

Bürkholz, A., Droplet Separation, VCH Verlagsgesellschaft, Weinheim—New York—Basle—Cambridge, 1989.

* cited by examiner

*Primary Examiner* — Karl J Puttlitz
(74) *Attorney, Agent, or Firm* — Donald R. Palladino

(57) ABSTRACT

Isocyanates are produced by reacting a primary amine with phosgene in the gas phase. In this process, the amine is vaporized and then superheated prior to introduction into the reactor. The amine is superheated to a temperature at least 10° C. above dew point before entry into the reactor. A pressure difference between the vaporizer and entry into the reactor of from 1 to 500 mbar is maintained.

9 Claims, No Drawings

PROCESS FOR THE PREPARATION OF ISOCYANATES IN THE GAS PHASE

The present invention relates to a process for the preparation of isocyanates from amines and phosgene in the gas phase.

Isocyanates, and in particular diisocyanates, are prepared in large amounts and serve chiefly as starting substances for the preparation of polyurethanes. They are usually prepared by reaction of the corresponding amines with phosgene. The reaction of the amines with phosgene can be carried out in the liquid phase, in the gas phase or by phosgenation of an amine spray prepared by atomization.

The present invention relates exclusively to phosgenation in the gas phase.

This process procedure is distinguished in that the reaction conditions are chosen such that at least the reaction components amine, isocyanate and phosgene, but preferably all the educts, products and reaction intermediate products, are gaseous under the reaction conditions chosen. Advantages of gas phase phosgenation are, inter alia, a reduced phosgene hold-up, the avoidance of intermediate products which are difficult to phosgenate and increased reaction yields.

Various processes for the preparation of diisocyanates by reaction of diamines with phosgene in the gas phase are known from the prior art.

EP 289 840 B1 discloses for the first time a process for the preparation of aliphatic diisocyanates by phosgenation of the corresponding diamines in the gas phase, in which the vaporous diamines, optionally diluted with an inert gas or with the vapours of an inert solvent, and phosgene are heated separately from one another to temperatures of from 200 to 600° C. and are reacted with one another continuously in a reaction space heated to 200 to 600° C. The absolute pressure here in the feed lines to the reaction space is 200 to 3,000 mbar, and at the exit from the reaction space is 150 to 2,000 mbar. The specification does not disclose the pressure under which the vaporization of the diamines is carried out and the time within which they are fed to the reaction space.

EP 593 334 B1 describes for the first time a process for the preparation of aromatic diisocyanates in the gas phase. According to this invention, the temperature which prevails in the reactor in which the phosgenation reaction is effected is between 250 and 500° C. The preheating temperature here for participants in the reaction is of the same order of magnitude as that required for carrying out the phosgenation. The pressure prevailing in the reactor is between 0.5 and 1.5 bar. Information regarding the pressure under which the vaporization of the diamines is carried out and the time within which they are fed to the reaction space is not given.

EP 570 799 B1 discloses a process for the preparation of aromatic diisocyanates by reaction of corresponding diamines with phosgene in the gas phase, characterized in that the phosgene and diamine are reacted above the boiling point of the diamine within an average dwell time of from 0.5 s to 5 s. For this, the vaporous diamines, optionally diluted with an inert gas or with the vapours of an inert solvent, and phosgene are heated separately to temperatures of from 200 to 600° C. and mixed continuously. The absolute pressure here is 200-3,000 mbar in the feed lines to the reaction space and 150-2,000 mbar downstream of the condensation stage of the reactor, according to the teaching of this specification maintaining this pressure difference leads to the directed flow being ensured in the reactor. The specification does not disclose the pressure under which the vaporization of the amine is carried out.

For the overall pressure in the reaction space of the reaction of phosgene and diamine, WO 2008/055898 A1 discloses a range of absolute pressures of from 0.1 to less than 20 bar, preferably 0.5 to 15 bar, and particularly preferably between 0.7 and 10 bar. The pressure here directly upstream of the mixing device is higher than the abovementioned pressure in the reactor. This pressure decreases, depending on the choice of the mixing device. Preferably, the pressure in the feed lines is 20 to 2,000 mbar, particularly preferably from 30 to 1,000 mbar higher than in the reaction space. The specification does not disclose the pressure under which the vaporization of the amine is carried out.

In addition to the reaction conditions, the nature and manner of the vaporization of the amines employed in the reaction with phosgene in the gas phase is also the subject matter of processes disclosed.

According to the above prior art, for the purpose of gas phase phosgenation the starting amines are vaporized and heated to 200 to 600° C., before they are led together with the phosgene into a reaction space in which a pressure of from 0.1 to less than 20 bar prevails. These reaction conditions disclosed in the prior art span a wide range and give no concrete indications of the conditions under which the starting amine should be vaporized, since in particular not all combinations from the ranges mentioned are suitable for vaporization of amines, since many amines which are suitable for gas phase phosgenation cannot be vaporized e.g. under 20 bar at 200° C.

Individual indications of the conditions under which the starting amine should be vaporized relate to the exposure of the amine to heat and the content of drops of liquid in the vaporized amine stream.

The exposure of the amines employed in the gas phase phosgenation to heat is addressed by EP 1 754 698 A1 by making use of a specific vaporizer technique. According to the teaching of EP1 754 698 A1, firstly the deposits to be observed in the reactor for reaction of the amines employed with phosgene are caused by the decomposition, during the reaction, of the amines employed. Secondly, long dwell times in the vaporization and superheating lead to a partial decomposition of the amines employed, ammonia being split off. This partial decomposition with splitting off of ammonia during the vaporization which is to be observed specifically if aliphatic amines are employed not only reduces the yield, but deposits of ammonium chloride also form during the subsequent phosgenation reaction and in the downstream pipelines and apparatuses. The installations must then be cleaned relatively frequently, corresponding production losses arising. As a technical solution, this specification discloses suppressing the splitting off of ammonia during the vaporization by employing specific milli or micro heat exchangers for the vaporization and superheating of the aliphatic amines. The specification discloses that by employing the heat exchangers disclosed with a very high volume-specific heat exchanger surface, the exposure of the amines to heat in the vaporization apparatuses can be reduced due to reduced film thicknesses. In these apparatuses, the heating, vaporization and superheating of the amine can be carried out here in each case under pressures of from 500 to 2,500 mbar, in each case within dwell times of from 0.001 to 60 s or 0.0001 to 10 s. Criteria for the superheating of the diamine and the time within which the vaporous diamine is fed to the reaction space are not mentioned, since merely dwell times for individual apparatuses are to be found in the specification.

The very small channels are a disadvantage of the micro heat exchangers disclosed in the specification EP 1 754 698 A1, so that very small amounts of solids, which are always present in industrial processes, already lead to a blockage and therefore reduce the service life of the vaporizer. It is furthermore a disadvantage of the total vaporization disclosed for the amines that the amines should not contain non-vaporizable constituents, because these are otherwise necessarily deposited as a solid residue on the vaporizer surface and therefore impair the heat transfer and finally lead to blocking of the vaporizer. However, the provision of amines in the required quality is very involved and expensive in the industrial process. The service life of the reactor is therefore indeed improved by the teaching of this specification, but the service life of the vaporizer system is impaired significantly, so that the total service life of the production installation is not advantageously improved.

To evaluate a stream obtained by vaporization, the person skilled in the art generally makes a distinction between vapour and gas. The person skilled in the art furthermore makes a distinction between boiling temperature and dew temperature in this connection. A liquid starts to vaporize on heating up to the boiling point and by additional feeding in of the energy needed for the vaporization. A vapour phase is obtained here above the liquid, and is in equilibrium with this. The vapour phase obtained above the boiling liquid here is at the dew point, i.e. the temperature at which condensation of the vapour starts, with formation of liquid. If e.g. a cold place is present or the temperature of the vapour cools only slightly, the vapour will therefore condense. For the person skilled in the art, a vaporous stream is thus characterized in that a slight lowering of temperature—such as can never be avoided completely on an industrial scale e.g. due to heat bridges or imperfect insulation—already leads to condensation and therefore to the formation of a liquid phase.

A gas, on the other hand, is characterized in that on cooling of a gas, the gas temperature is initially only reduced, without the temperature here falling below the dew temperature and without condensation and formation of a liquid phase therefore occurring. Only when the gas temperature is lowered further to the dew temperature does condensation start, a liquid phase is formed and the vapour region is reached.

In industrial vaporization apparatuses, in addition to the generally applicable liquid-vapour equilibrium, there is also the effect that drops of liquid are torn out of the liquid by the action of the vaporizing material, i.e. droplets are carried along and as a result are likewise additionally in the vapour phase. The droplets carried along in general have a size of up to 1,000 µm. Due to this effect, a gas phase above the dew temperature can therefore also contain droplets. This is to be observed in particular where closed films of liquid travel upwards, e.g. at the base of falling film vaporizers or during nucleate boiling within boiler vaporizers.

The drop content in the vaporous diamine stream has already been the subject matter of earlier considerations. According to EP 1 935 876 A1, the vaporous amines are said to contain essentially no droplets of non-vaporized amines, that is to say a maximum of 0.5 wt. % of the amine, and in particular a maximum of 0.05 wt. % of the amine, based on the total weight of the amine, is in the form of non-vaporized droplets and the remaining part of the amine is in vaporous form. Very particularly preferably, according to the teaching of EP 1 935 876 A1 the vaporous amines are said to contain no droplets of non-vaporized amines. According to EP 1 935 876 A1, the reactor running time is increased significantly by generation of an essentially drop-free vaporous diamine stream before entry into the reactor. According to the teaching of this specification, this can be achieved by incorporating drop separators between the vaporization and superheating systems and/or by the vaporization apparatuses also having the function of a drop separator. Suitable drop separators are described e.g. in "Droplet Separation", A. Bürkholz, VCH Verlagsgesellschaft, Weinheim—New York—Basle—Cambridge, 1989. EP 1 935 876 A1 mentions drop separators which cause a low pressure loss as particularly preferred. The teaching of this specification for the person skilled in the art is therefore that the vaporization of the amine is followed by a drop separator with the lowest possible pressure loss, a vaporous amine stream being obtained, in order to achieve a long service life of the gas phase reaction.

However, the process disclosed is disadvantageous in particular for carrying out the gas phase phosgenation on a large industrial scale, since the pressure loss of drop separators increases very sharply with the volume flow rate. Furthermore, the degree of separation, i.e. the content of the droplets separated off by the drop separator, is lower with a high volume flow rate than with a low volume flow rate under the same pressure loss. According to the teaching of EP 1 935 876 A1, for a large-scale industrial procedure either drop separators with a low degree of separation would therefore have to be used in order to minimize the pressure loss caused by the separator. The vapour stream would therefore no longer be drop-free—with the known disadvantages for the service life of the gas phase reaction. Or drop separators with a high degree of separation would have to be used in order to generate the drop-free amine stream necessary according to the teaching of the prior art, but these cause a high pressure loss.

According to EP 1 754 698 B1, however, an increased pressure loss in the stream of the vaporous amine is a disadvantage in the large-scale industrial procedure, since due to the increase in pressure in the vaporizer the boiling temperature rises and the increase in the temperature required for the vaporization can have the effect of more ammonia being split off from the diamine, which in turn leads to blocking of the gas phase reactor due to the formation of ammonium chloride and therefore shortens the service life of the gas phase reaction.

A high pressure loss is furthermore also a disadvantage because a high pressure difference leads to a higher gas speed of the vaporous, drop-containing diamine stream, a high gas speed of a gas stream laden with drops of liquid being a disadvantage since abrasion may occur on the pipelines as a result.

The person skilled in the art therefore deduces from the prior art of gas phase phosgenation the general teaching that the vaporization of diamines results in a drop-containing vapour stream which must be led over a drop separator, which causes a pressure loss, in order to achieve an advantageous absence of drops in this way, it being necessary at the same time for a technical solution to be found for the disadvantages associated with the pressure loss (increase in the boiling point of the diamine, abrasion in the pipelines).

When the process is carried out in practice on a large industrial scale, according to the prior art an essentially drop-free amine stream can be generated only at the expense of a high pressure loss between the amine vaporization and the reaction, as a result of which the adverse consequences from the prior art for the service life of a gas phase reaction unavoidably follow, since a high pressure loss between the reactor and the amine vaporization means a high vaporization pressure and therefore an increased vaporization temperature. None of the specifications disclosed to date is concerned with these problems, and a solution to them is therefore not to be deduced from the prior art.

The object of the invention was therefore to provide a process for the large-scale industrial preparation of isocyanates by phosgenation in the gas phase, which is distinguished in that the amine stream led to the reactor is to the greatest extent drop-free and at the same time the pressure difference between the amine vaporization and the reactor is low.

It has now been found, surprisingly, that an absence of drops in the diamine stream which is advantageous for the gas phase phosgenation on a large industrial scale is also achieved if the pressure in the vaporizer is only at most 500 mbar higher than in the reactor, and at the same time the diamine stream leaving the vaporizer is fed with an average dwell time of more than 0.01 s to the reactor for the reaction such that at the entry into the reactor the diamine stream has a temperature of at least 10° C. above the dew point.

The limitation of the pressure loss between the vaporizer and the reactor restricts the choice of possible apparatuses for the drop separation, but brings the advantages of a low diamine boiling point and low gas speeds. In one possible embodiment of the process according to the invention, the use of apparatuses for drop separation is dispensed with completely.

The associated restrictions in the drop separation can be accepted on the basis of the inventive novel process procedure.

It has been found, surprisingly, that the separation of droplets out of the diamine stream does not have to take place or does not have to take place to the full extent by drop separators which cause a pressure loss. Rather, a long reactor service life can also be achieved without complete drop separation, which would cause a high pressure loss, if the dwell time and increase in temperature above the dew point of the diamine stream before entry into the reactor are sufficient for the droplets present in the vapour stream after the vaporization to be vaporized completely by the time of entry into the reactor. The invention therefore provides a process in which an amine stream which is to the greatest extent drop-free is passed to the reactor, and furthermore on the basis of the low pressure difference between the reactor and the amine vaporization a low amine boiling temperature is obtained. The present invention therefore solves the problem that both a low amine boiling temperature and an amine stream to the reactor which is to the greatest extent drop-free are necessary for a long running time of a gas phase reaction.

The invention therefore provides a process for the preparation of isocyanates by reaction of primary amines with phosgene in the gas phase, in which a) the primary amine is vaporized in a vaporizer, and b) the vaporized amine obtained in step a) exits from the vaporizer and is passed via a feed to the reactor and introduced into the reactor, characterized in that c) the vaporized amine obtained in step a) is superheated in the feed to the reactor, so that it has a temperature of at least 10° C. above the dew point in the feed directly before entry into the reactor, and d) the dwell time of the vaporized amine in step b) is more than 0.01 second, and e) the pressure difference over the feed between the exit from the vaporizer and the entry into the reactor is between 1 and 500 mbar.

In a preferred embodiment of the present invention, for the purpose of the gas phase phosgenation the diamine is vaporized in at least one vaporizer and heated to temperatures of from 200 to 600° C., preferably 200 to 500° C., particularly preferably 250 to 450° C., and optionally fed to the reaction space in a form diluted with an inert gas, such as $N_2$, He or Ar, or with the vapours of an inert solvent, e.g. aromatic hydrocarbons, optionally with halogen substitution, such as e.g. chlorobenzene or ortho-dichlorobenzene.

Any desired suitable vaporizers can in principle be employed as vaporizers for the amine vaporization. Tube bundle heat exchangers, plate heat exchangers or falling film vaporizers, optionally with pumped circulation, can preferably be employed. Micro heat exchangers or micro vaporizers as described in WO 2005/016512 A or in DE 10 2005 036870 A1 can also be employed.

Preferably, vaporization systems in which a small work content is led with a high circulating output over a falling film vaporizer are employed. To minimize the exposure of the diamines to heat, the vaporization operation—as stated above—is optionally assisted by feeding in inert gas and/or solvent vapours.

In the process according to the invention, both the vaporization and the superheating can be carried out in one stage, but they can also each be carried out in several stages. After the first or, where appropriate, the only superheater, the vaporous diamine stream can be led through a drop separator, in particular through a drop separator with a drop diameter limit of from 5 to 550 µm, preferably 10 to 100 µm. Alternatively, it is also possible, after the vaporizer, for the vaporous diamine stream to be led through a drop separator, in particular through a drop separator with a drop diameter limit of from 5 to 550 µm, preferably 10 to 100 µm. The drop separators preferably have a low pressure loss, but a maximum pressure loss such that the pressure loss between the exit from the vaporizer and the entry into the reactor is between 1 and 500 mbar.

According to the invention, after the vaporization the vapour stream obtained from the vaporization is superheated in the feed to the reactor so that directly before entry into the reactor the gas has a temperature of at least 10° C., preferably of at least 15° C. and very particularly preferably of at least 25° C. above the dew point. By the transportation of the drops of liquid which have not been separated off in the diamine stream superheated in this way, the droplets absorb energy from the surrounding hot gas and vaporize. The nature of the superheating is not essential to the invention, and it can be effected e.g. by an apparatus such as e.g. a tube bundle heat exchanger or by a heated pipeline. In a specific embodiment, the superheater with which the vaporized amine is superheated to a temperature of at least 10° C., preferably 15° C., very particularly preferably 25° C. above the dew point of the diamine also functions as a drop separator. In a particularly specific embodiment, this superheater has a liquid drain in order to ensure constant emptying of the drop separator.

Preferably, the vaporization in step a) is carried out under absolute pressures of between 0.1 and 20 bar.

The average dwell time from leaving the vaporizer to entry into the reactor is more than 0.01 second, preferably more than 0.1 and particularly preferably more than 0.5 second. In general, the dwell time before entry into the reactor is not more than 60 s. Technical measures here, e.g. adequate insulation to avoid radiation losses, or concomitant heating of the pipeline by means of heat transfer oil, flue gas or electrical concomitant heating, prevent the gas from cooling below the temperature limit according to the invention to the dew temperature on entry into the reactor.

It has been found, surprisingly, that by the combination of superheating of the gas by at least 10° C., preferably by at least 15° C. and very particularly preferably by at least 25° C. above the dew point before entry into the reaction in combination with a dwell time of more than 0.01 second, preferably more than 0.03 and particularly preferably more than 0.08 second in the stream which is obtained from the vaporization and still contains droplets, an amine gas stream to the reactor which is to the greatest extent drop-free can be obtained without the drop separators necessary according to the prior art, which cause a pressure loss, being necessary for this.

By the process according to the invention, the pressure difference between the entry into the reactor and the amine vaporization can be limited to not more than 500 mbar. In general, a pressure difference of more than 1 mbar is necessary, preferably more than 10 mbar and particularly preferably of more than 20 mbar, in order to obtain an adequate flow rate of the gas. Preferably, the pressure difference between the entry into the reactor and the amine vaporization is not more than 450 mbar, particularly preferably not more than 400 mbar.

This means that the pressure in the amine vaporization is not more than 500 mbar above the pressure at the entry into the reactor. As a result, the boiling temperature of the amine is kept low, and the disadvantages from the decomposition of the amine at an elevated boiling temperature which are described from the prior art can be avoided. The low pressure difference therefore has a positive effect on the service life of the gas phase reaction.

By adhering to the requirements described above for the dwell time in the feed according to step b) and superheating, an essentially drop-free vaporous diamine stream is obtained with a low pressure loss and therefore low vaporization temperature before entry into the reactor, and as a result the reactor running time is increased significantly. An essentially drop-free vaporous stream of starting amine is understood as meaning that the vaporous amine essentially contains no droplets of non-vaporized amines, that is to say that a maximum of 0.5 wt. % of the amine, particularly preferably a maximum of 0.05 wt. % of the amine, based on the total weight of amine, is present in the form of non-vaporized droplets and the remaining part of the amine is present in vaporous form. Very particularly preferably, the vaporous amines contain no droplets of non-vaporized amines.

The vaporizers and/or superheaters and the pipelines for generation of the vaporous diamine stream to the gas phase reactor can be produced from any desired metallic material, e.g. steel, high-grade steel, titanium, Hastelloy, Inconel or other metallic alloys. Metallic materials with a low nickel content are preferably used. Furthermore, the pipelines preferably have a gradient towards the bottom of the vaporizer over their entire length, but at least partially, so that any condensate obtained can flow back into the vaporizer.

If the diamine stream already has a drop size distribution after the vaporizer or the superheater such that the droplets present essentially can be vaporized by the hot gas stream under the given dwell times and temperatures, the drop separator or separators can even be dispensed with completely, which additionally has the effect of reducing the pressure loss between the vaporizer and reactor.

The reaction according to the invention of the primary amine with phosgene is carried out in a reactor. The reactor contains at least one reaction space. Reaction space is understood as meaning the space in which the mixing and the reaction of the educts and intermediate products take place, since because of the high speed of the gas phase reaction, mixing and reaction can scarcely be separated spatially in the process according to the invention. Reactor is understood as meaning the technical device which contains the reaction space. A reactor here can also contain several reaction spaces.

The process according to the invention can in principle be applied to any reaction space and reactor geometry.

In a further preferred embodiment of the process according to the invention, the reactor has, after the reaction space in which, after mixing of the educts, a conversion of the amine groups into the isocyanate groups of 80%, preferably 90%, particularly preferably 99%, very particularly preferably 99.5% is achieved, a rotationally symmetric reaction space with a constant and/or widened flowed-through cross-sectional area.

The process according to the invention can in principle be applied to any procedure of gas phase phosgenation. The adiabatic procedure described in EP 1 935 876 A1 is preferred. However, the process described can also be applied to an isothermal procedure.

The dwell time chosen for reaction of the amine groups with the phosgene to give the isocyanate is between 0.05 and 15 seconds, depending on the nature of the amine employed, the start temperature, where appropriate the adiabatic increase in temperature in the reaction space, the molar ratio of amine employed and phosgene, the nature and amount of the at least one inert substance and the reaction pressure chosen.

In the process according to the invention, it is advantageous to employ phosgene in excess with respect to the amine groups to be reacted. Preferably, a molar ratio of phosgene to amine groups of from 1.1:1 to 20:1, preferably 1.2:1 to 5:1 is present. The phosgene is also heated to temperatures of from 200 to 600° C. and optionally fed to the reaction space in a form diluted with an inert gas, such as $N_2$, He or Ar, or with the vapours of an inert solvent, e.g. aromatic hydrocarbons, without or with halogen substitution, such as e.g. chlorobenzene or o-dichlorobenzene.

After the phosgenation reaction has taken place in the reaction space, the gaseous reaction mixture, which preferably comprises at least one isocyanate, phosgene, optionally an inert substance and hydrogen chloride, is preferably freed from the isocyanate formed. This can be carried out, for example, by subjecting the reaction mixture continuously leaving the reaction space to a condensation in an inert solvent, as has already been recommended for other gas phase phosgenations (EP 0 749 958 A1).

Preferably, however, the condensation is carried out by a procedure in which the reaction space employed in the process according to the invention has at least one zone into which one or more suitable streams of liquid ("quench liquids") are sprayed for discontinuation of the reaction of the amines employed and the phosgene to give the corresponding isocyanates. By this means, as described in EP 1 403 248 A1, rapid cooling of the gas mixtures can be carried out without the use of cold surfaces.

In a particularly preferred form of the process according to the invention, the at least one zone (cooling zone) is integrated into a quenching stage, such as has been disclosed e.g. in EP 1 403 248 A1. In a particularly preferred form, several cooling zones are employed. Integration and operation of these at least two cooling zones are preferably effected with a quenching stage. This is disclosed with respect to construction and operation in EP 1 935 875 A1.

Instead of the integrated combination of the at least one cooling zone of a reactor with a quenching stage, such as has been disclosed in EP 1 935 875 A1, the corresponding integrated combination of the cooling zones of several reactors with a quenching stage is likewise possible. Preferably, however, the integrated combination of a reactor with at least one cooling zone with a quenching stage is preferred.

The gas mixture leaving the condensation or quenching stage is preferably freed from residual isocyanate in a downstream gas wash with a suitable wash liquid, and is preferably then freed from excess phosgene in a manner known per se. This can be carried out by means of a cold trap, absorption in an inert solvent (e.g. chlorobenzene or dichlorobenzene) or by adsorption and hydrolysis on active charcoal. The hydrogen chloride gas passing through the phosgene recovery stage can be recycled in a manner known per se for recovery of the chlorine required for the phosgene synthesis. The wash liquid obtained after its use for the gas wash is then preferably at least partially employed as the quench liquid for cooling the gas mixture in the corresponding zone of the reaction space.

The isocyanates are subsequently preferably prepared in a pure form by working up the solutions or mixtures from the condensation or quenching stage by distillation.

In the process according to the invention, those primary aromatic amines, and in particular those diamines, which can be converted into the gas phase essentially without decomposition are preferably employed.

Examples of preferred aliphatic or cycloaliphatic diamines are 1,4-diaminobutane, 1,6-diaminohexane (HDA), 1,11-diaminoundecane, 1-amino-3,5,5-trimethyl-3-aminomethylcyclohexane (IPDA), 4,4'-diaminodicyclohexylmethane or 4,4'-diaminodicyclohexyl-2,2-propane. However, diamines of the abovementioned type with exclusively aliphatically or cycloaliphatically bonded amino groups are particularly preferred, such as isophoronediamine (IPDA), hexamethylenediamine (HDA) or bis(p-aminocyclohexyl)methane (PACM 20).

Examples of preferred aromatic diamines are toluylenediamine (TDA), in particular 2,4-TDA and 2,6-TDA and mixtures thereof, diaminobenzene, naphthyldiamine (NDA) and 2,2'-, 2,4'- or 4,4'-methylenediphenyldiamine (MDA) or isomer mixtures thereof. Toluylenediamine (TDA), in particular 2,4-TDA and 2,6-TDA and mixtures thereof, is particularly preferred. 2,4-/2,6-TDA isomer mixtures with isomer ratios of 80/20 and 65/35 are very particularly preferred.

EXAMPLES

A. Example According to the Invention

A TDA stream of 2,500 kg/h is vaporized at a temperature of 315° C., led through a drop separator with a drop diameter limit of 530 μm and fed to the reactor. On exit from the drop separator, the stream contains 10 wt. % of non-vaporized droplets. The feed to the reactor is such that after exit from the vaporization the stream is superheated, the stream being heated to 15° C. above the dew point on entry into the reactor. The dwell time of the gas in the feed to the reactor is 4.1 seconds. The droplets initially present vaporize here, so that the stream to the reactor is essentially drop-free. The pressure difference between the vaporization and the entry into the reactor is less than 500 mbar.

B. Example According to the Invention

A TDA stream of 2,500 kg/h is vaporized at a temperature of 315° C., led through a drop separator with a drop diameter limit of 100 μm and fed to the reactor. On exit from the drop separator, the stream still contains 10 wt. % of non-vaporized droplets. The feed to the reactor is such that after exit from the vaporization the stream is superheated, the stream being heated to 15° C. above the dew point on entry into the reactor. The dwell time of the gas in the feed to the reactor is 0.7 second. The droplets initially present vaporize here, so that the stream to the reactor is essentially drop-free. The pressure difference between the vaporization and the entry into the reactor is less than 500 mbar.

What is claimed is:

1. A process for the production of an isocyanate comprising reacting a primary amine with phosgene in a reactor in the gas phase the process comprising the following steps:
   (a) vaporizing the amine in a vaporizer, the vaporized amine containing droplets,
   (b) superheating the vaporized amine in a feed to the reactor to a temperature at least 15° C. above dew point in the feed directly before entry into the reactor, wherein either (i) no device for drop separation is included in the feed to the reactor, or (ii) a drop separator which has a drop diameter limit of from 5 to 550 micron is arranged in the feed to the reactor,
   (c) allowing the vaporized amine to remain in the feed to the reactor for a dwell time of more than 0.08 seconds,
   (d) maintaining a pressure difference between exit of the vaporizer and entry into the reactor of from 1 to 500 mbar, and
   (e) introducing the superheated amine into the reactor via the feed.

2. The process of claim 1 in which the amine is toluene diamine, phenyldiamine, naphthyldiamine, methylene diphenyldiamine, hexamethylene diamine and/or isophorone diamine.

3. The process of claim 1 in which the dwell time of the vaporized amine in the feed is greater than 0.1 second.

4. The process of claim 1 in which (a) is carried out in the presence of an inert gas and/or in the presence of vapors of an inert solvent.

5. The process of claim 1 in which (a) is carried out at an absolute pressure of from 0.1 to 20 bars.

6. The process of claim 1 in which an after-heater is included in the feed and the vaporized amine is heated to a temperature of from 200 to 600° C.

7. The process of claim 1, wherein a drop separator which has a drop diameter limit of from 5 to 550 micron is arranged in the feed to the reactor.

8. The process of claim 1, wherein the primary amine is a primary aromatic amine.

9. The process of claim 8, wherein the primary aromatic amine is toluene diamine.

* * * * *